(12) United States Patent
Wong et al.

(10) Patent No.: US 9,726,601 B1
(45) Date of Patent: Aug. 8, 2017

(54) NDIR INTERFERENCE CONTROL IN LIQUIDS

(71) Applicant: Airware, Inc., Goleta, CA (US)

(72) Inventors: Jacob Y Wong, Goleta, CA (US); Thomas Campbell, Newbury Park, CA (US)

(73) Assignee: AIRWARE, INC., Goleta, CA (US)

( * ) Notice: Subject to any disclaimer, the term of this patent is extended or adjusted under 35 U.S.C. 154(b) by 0 days.

(21) Appl. No.: 15/594,418

(22) Filed: May 12, 2017

Related U.S. Application Data

(63) Continuation of application No. 15/444,136, filed on Feb. 27, 2017, which is a continuation-in-part of application No. 15/358,873, filed on Nov. 22, 2016, now Pat. No. 9,606,053.

(51) Int. Cl.
*G01N 21/3504* (2014.01)
(52) U.S. Cl.
CPC .............................. *G01N 21/3504* (2013.01)

(58) Field of Classification Search
CPC .......................... G01N 21/3504; G01N 33/49
See application file for complete search history.

(56) References Cited

U.S. PATENT DOCUMENTS 6,509,567 B2 * 1/2003 Boudet ................. G01M 3/002
250/343

* cited by examiner

*Primary Examiner* — Mark R Gaworecki
(74) *Attorney, Agent, or Firm* — Roy Landerson

(57) ABSTRACT

NDIR is used to determine a concentration of a chosen molecule M in a liquid sample which contains one or more interfering molecules $M_J$ which absorb radiation at the signal wavelength used in the NDIR process by addition of an interference source. M is calculated by electronics which use $R_{ave}(t)$ from a pulsed signal and reference channel output and a calibration curve which is validated by use of $R_{Jave}(t_2)$ from a pulsed interference and reference channel output. Signal, interference and reference sources are pulsed at a frequency which is sufficiently fast so that a given molecule of M or $M_J$ will not pass in and out of the liquid sampling matrix within the pulsing frequency.

9 Claims, 9 Drawing Sheets

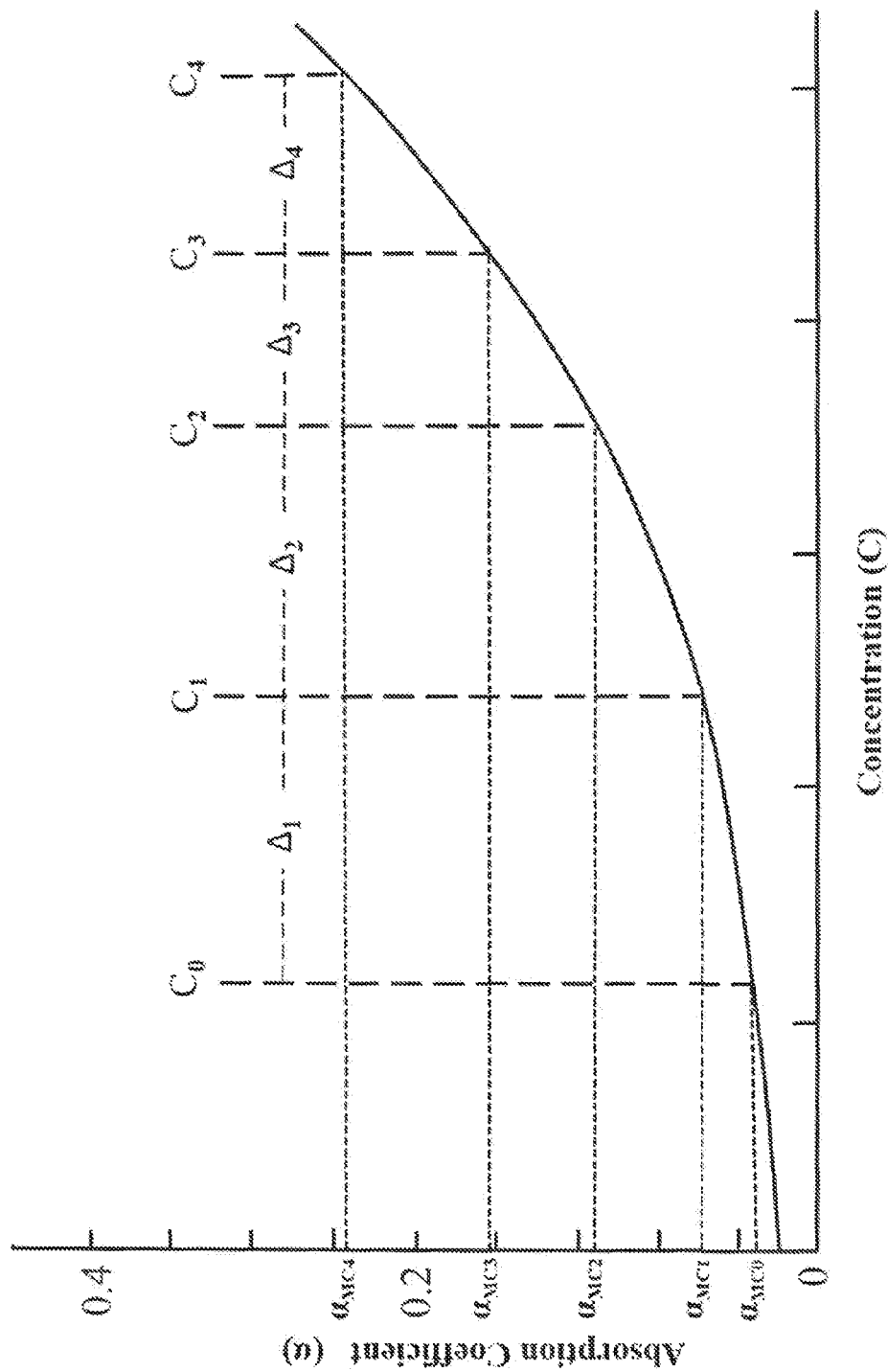

NDIR INTERFERENCE CONTROL IN LIQUIDS

CROSS-REFERENCE TO RELATED APPLICATIONS

The present invention is a continuation-in-part application of U.S. Ser. No. 15/444,136, filed Feb. 27, 2017, which is a continuation-in-part application of U.S. Ser. No. 15/358,873, filed Nov. 22, 2016, which was issued on Mar. 28, 2017 as U.S. Pat. No. 9,606,053, the disclosures of all of which are specifically incorporated herein by reference.

FIELD OF THE INVENTION

The present invention relates to noise reduction in the measurement of particles in liquid via Non-Dispersive Infra-Red (NDIR) technique.

BACKGROUND OF THE INVENTION

Non-Dispersive Infra-Red (NDIR) is a common measurement principle for detecting gases in the environment. NDIR sensors utilize the principle that various gases exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating, for isolating for the purpose of measurement the radiation in a particular wavelength band that coincides with a strong absorption band of a gas to be measured.

NDIR has enjoyed widespread use in gas measurement because NDIR gas sensors are highly accurate, relatively stable and easy to operate and maintain.

The present invention is concerned with addressing problems arising from use of NDIR to detect molecules in a liquid medium, rather than in gas.

SUMMARY OF THE INVENTION

The present invention is generally directed to a process and apparatus useful for determining a sample concentration of a chosen molecule M in a liquid phase through use of NDIR when at least one interfering molecule $M_J$ absorbs radiation at the signal wavelength used in the NDIR process. To compensate for absorption by one or more interfering molecules $M_J$, a third source, called an interference source, is added. The signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band. The signal source, the interference source and the reference source are each pulsed at a preselected frequency of at least N Hz (e.g., 10 KHz or greater with a duty factor of at least 10%) which is sufficiently fast so that a given molecule of the targeted molecule M or interfering molecule $M_J$ will not pass in and out of the liquid sampling matrix within the preselected frequency. The signal, interference and reference sources are pulsed into a multiplexer and collimated into a pulsed beam which is directed through a sample space containing the liquid phase. A detector detects infrared radiation as a pulsed signal after it passes through the liquid phase and signal processing electronics is used to obtain two average ratio values of $R_{ave}(t)$ from the pulsed signal and reference channel output and $R_{Jave}(t_2)$ from the pulsed interference and reference channel output. $R_{Jave}(t_2)$ is used to determine that a calibration curve is valid for use in calculating the concentration of the targeted molecule M in the liquid sampling matrix by use of $R_{ave}(t)$ and the calibration curve and, if it is valid, such concentration is calculated and provided as an output from electronics.

Accordingly, it is an object of the present invention to provide an improved system and process for the measurement of chosen molecules in solution with interfering molecules via NDIR.

This and further objects and advantages will be apparent to those skilled in the art in connection with the figures and the detailed description of the invention set forth below.

BRIEF DESCRIPTION OF THE DRAWINGS

FIG. 9 shows the calibration curve for concentration of molecules M as a function of the absorption coefficient without the presence of absorption interference noise caused by interfering molecules.

DETAILED DESCRIPTION OF THE INVENTION

Figure 1:
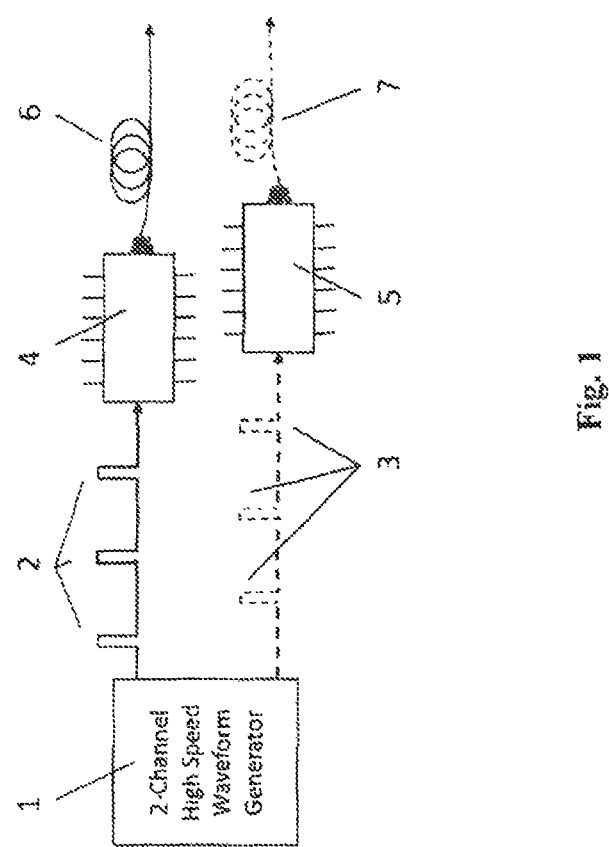
FIG. 1 illustrates how a Signal diode laser and the Reference diode laser are driven alternately and successively by a high speed waveform generator.

Because the present invention is concerned with addressing problems arising from use of NDIR to detect molecules in a liquid medium, rather than in gas, it is necessary to first review the inventive concepts that are disclosed in U.S. Pat. No. 9,606,053.

An NDIR sensor used to detect molecules in a gaseous phase typically utilizes an infrared source which sends radiation through a sample chamber to a detector which has a spectral filter that passes only radiation which coincides with the absorption band of the gas to be detected. The noise sources of such an NDIR sensor come mainly from the source, the detector and the temperature of the sensor environment.

Traditional NDIR technique uses a double beam configuration to reduce noise. A first channel, called a signal channel, uses an absorption wavelength chosen to detect a target gas and a first detector with a first filter coincident with the absorption of the target gas. A second channel, called a reference channel, uses a neutral wavelength (at which the target gas does not absorb) located close to the absorption wavelength with a second detector with a second filter which is in no way coincident with the absorption of the target gas. Because there are two different detectors, with radiation emanating from the same source, the signal and reference channels have two difference beam paths. The theory is that the signal channel is equally affected by all non-gas phenomena which might introduce noise as the signal channel, so by taking the ratio of the outputs of the two channels, namely the signal and reference channels, one can minimize all the noise-causing factors inevitably present in the sensor. So, ideally, only the presence of the target gas in the optical path will affect the ratio. The reason why the double beam configuration works so well in noise reduction is because particles in a gas phase are very well separated from one another with lots of space between them.

Gas molecules typically move around very fast and have a molecular speed in the neighborhood of ~500 m/s. Consequently, at any particular instinct, only a very small number of molecules (including those that are targeted for detection) find themselves in between the source and the detectors. It is because of this particular particle environment that extraneous noise due to unwanted scattering is found to be very small and can be neglected when compared with other traditional noise sources.

If one wishes to use NDIR to detect molecules in liquid, a new source of noise will be introduced, namely, via scattering due to the difference between molecular densities in a gas phase versus that in a liquid phase. Whereas the scattering of source radiation by molecules lying between the source and the detectors is not a significant source of noise in a gaseous medium due to the large amount of free space between molecules, it can become a significant source of noise in a liquid phase where free space between molecules is greatly reduced.

Because of the different particle environment prevailing in the gas and liquid phases, the NDIR absorption technique for the detection of particles works well in the gas phase but not in the liquid phase. In order to solve this problem, the present invention takes an unprecedented approach to come up with a method and apparatus that makes the NDIR absorption technique work in the liquid phase very much like in the gas phase. The same double beam configuration of the traditional NDIR absorption technique is followed which includes the use of a second channel operating at a neutral wavelength just off that of the signal channel. By processing the ratio of the signal outputs from the two channels, namely the signal and the reference, some of the error-causing factors affecting the performance of the sensor will be eliminated, as expected, just as they are similarly eliminated when using the same technique in a gas phase. The additional and unique feature of the present method is to provide a sensor hardware configuration in which both the signal and the reference beams encounter almost exactly the same particle environment during measurement. This is accomplished by executing the following four steps.

Step one is to operate the signal beam and the reference beam separately, each with its own pulsed source. Furthermore, the sources of both beams are pulsed at the same and a very high frequency rate typically greater than 10 KHz with a duty factor around 20-25%. Because of this high pulse frequency requirement, only semiconductor LED and/or diode laser sources will be satisfactory.

Step two is to time the outputs of the signal and reference sources in such a way so that they are turned on alternately and sequentially one at a time, and, in an especially preferred embodiment, separated by no more than one-half of their pulsing period in time. Furthermore, the outputs of these two sources are optically combined via a multiplexer or other means that performs the same function so that both the signal and the reference beams physically traverse the same space of liquid matrix before being detected by a single infrared detector. The detector is required to have a response time fast enough to adequately generate the correct signal outputs from the rapidly incident radiation pulses from the signal and the reference beams.

Step three is to choose the wavelength of the signal and the reference channels. The choice of the wavelength for the signal channel has to be coincident with the absorption band of the target particle to be measured. The wavelength for the reference channel has to be neutral but just off the absorption and as close to it as possible but in no way coincident with it. This way of choosing the wavelength for the reference channel has to do with making sure that the same particle environment for purposes of scattering is almost the same for both the signal beam and the reference beam (if their wavelengths are almost the same). This is because of the fact that elastic scattering is a function of the wavelengths of the radiation in the incident beams.

Step four is processing the data received by the detector and explains how the calibration procedures are carried out in order to obtain the concentration level of the particles in the liquid. When the Signal beam and the Reference beam are alternately and successively pulsed at N Hz (N>$10^4$), a ratio value "R" is calculated for each generated Signal channel output and the corresponding Reference channel output, namely R=Signal/Reference. At the pulse rate of N Hz, there will be N such ratio values generated every second. For a preselected pulsing time period of "t", where "t" is in seconds, there will be N×"t" ratio values generated. The average value of R over this time period "t", namely $R_{ave}(t)$, is calibrated against the concentration of particles in the liquid. Thus the value of $R_{ave}(t)$ obtained by using a signal processing technique for analyzing the detector outputs yields the concentration level of the particles in the liquid.

The present invention takes advantage of the fact that although the density of molecules in the liquid phase is very high, the velocity of the molecules moving about in it is very slow, typically ~5 mm/sec. Thus, assuming that the cross-sectional area of the sampling matrix is of the order of a few $mm^2$, the time taken for molecules to move in and out of the sampling area many times is of the order of hundreds of milliseconds. Accordingly, if the measurement time between the Signal beam and the Reference beam is of the order of a few tenths of a millisecond, the particle environment traversed by both beams during the measurement can be considered as almost unchanged or substantially identical. In other words, since the particle environment for the Signal and the Reference channels during their respective measurement hardly changes when steps 1-4 described above for the liquid phase are executed, the phenomena of unwanted scattering should stay pretty much the same for both beams, with a resultant significant reduction and suppression of noise attributable to scattering arising from a liquid phase sampling environment.

FIGS. 1-4 schematically depict a specially designed apparatus that is used to implement the method of rendering the NDIR absorption technique workable in the liquid phase by suppressing unwanted scattering noise due to the presence of a large number of mobile particles in the liquid matrix between the source and the detector. As shown in FIG. 1, a 2-channel high speed waveform generator 1 (>10 KHz) is employed to generate alternately and successively voltage pulses 2 and 3 to drive, respectively, Signal diode laser 4 and Reference diode laser 5. As shown in FIG. 1, the outputs of both diode laser 4 and diode laser 5 are interfaced respectively to optical fibers 6 and 7. The narrow spectral output of Signal diode laser 4 is selected to coincide with the absorption band of the target particle to be detected in the liquid matrix. But the narrow spectral output of Reference diode laser 5 is selected to be off but close to the absorption band of the target particle in the liquid matrix to be detected.

Figure 2:
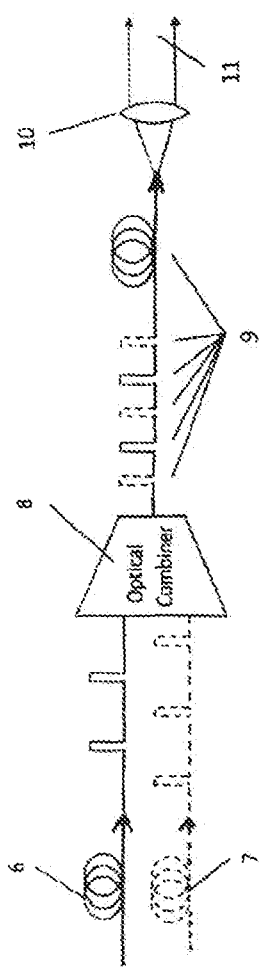
FIG. 2 illustrates how the outputs of the Signal diode laser and the Reference diode laser are combined into a single radiation beam alternately and successively representing both diode lasers via the use of an optical multiplexer.

FIG. 2 illustrates how outputs of the Signal laser beam 4 and Reference laser beam 5 are spatially combined into a single radiation beam before being focused onto the infrared detector. As shown in FIG. 2, output of the Signal laser beam 6 and output of the Reference laser beam 7 are combined in an optical multiplexer 8 to form a single radiation beam 9 before being collimated into a parallel beam 10 by collimating lens 11.

Figure 3:
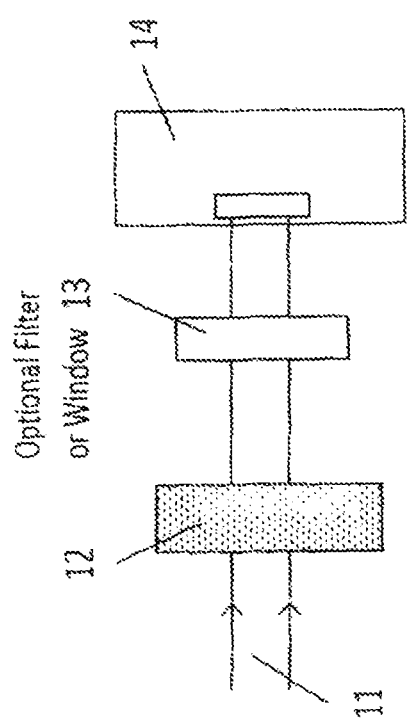
FIG. 3 illustrates the trajectory of the combined Signal and Reference diode laser beam to the infrared detector after passing through the sample chamber containing the liquid matrix and additional optional optical elements.

FIG. 3 illustrates how parallel radiation beam 10 (see FIG. 2) finds its way to the infrared detector. As shown in FIG. 3, single parallel beam 10 (which actually comprises both Signal laser beam 6 and Reference laser beam 7 being turned on alternately and successively by the 2-channel high speed waveform generator 1 of FIG. 1) first traverses sample chamber 12 containing the liquid matrix before being incident onto a TE-cooled infrared detector 14 after passing through an optional filter or window 13 for noise reduction (if needed).

Figure 4:
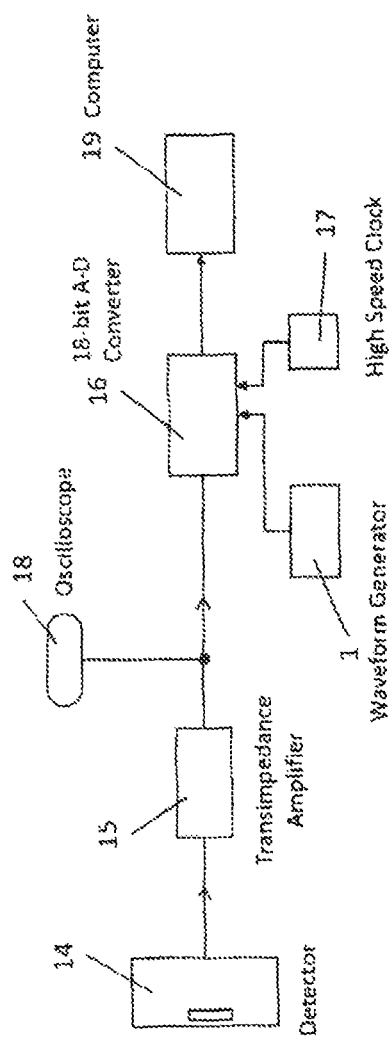
FIG. 4 illustrates the steps for transforming the analog infrared detector signal into digital data before inputting them into the computer for final data processing and analysis.

For signal processing as illustrated in FIG. 4, output of infrared detector 14 is first fed into a transimpedance amplifier 15 the output of which is inputted to an 18-bit Analog-to-Digital converter 16 triggered by waveform generator 1 (see FIG. 1) and a high speed clock 17. The analog signal can be monitored by an oscilloscope 18 before the digital signal is fed into a computer 19 for data analysis. Calculated ratio values are cross referenced to known compound concentration values. These compound concentration values can be reported individually to an output device such as a flat panel display. As values are collected over time, they can be plotted in a graphical format to illustrate trends over time. Running compound concentration values can be averaged over time, as one example, for smoother data tracking. Data output 20 can be sent from the detector electronics by wired or wireless interfaces such as Bluetooth or WiFi standards to external devices.

Figure 5:
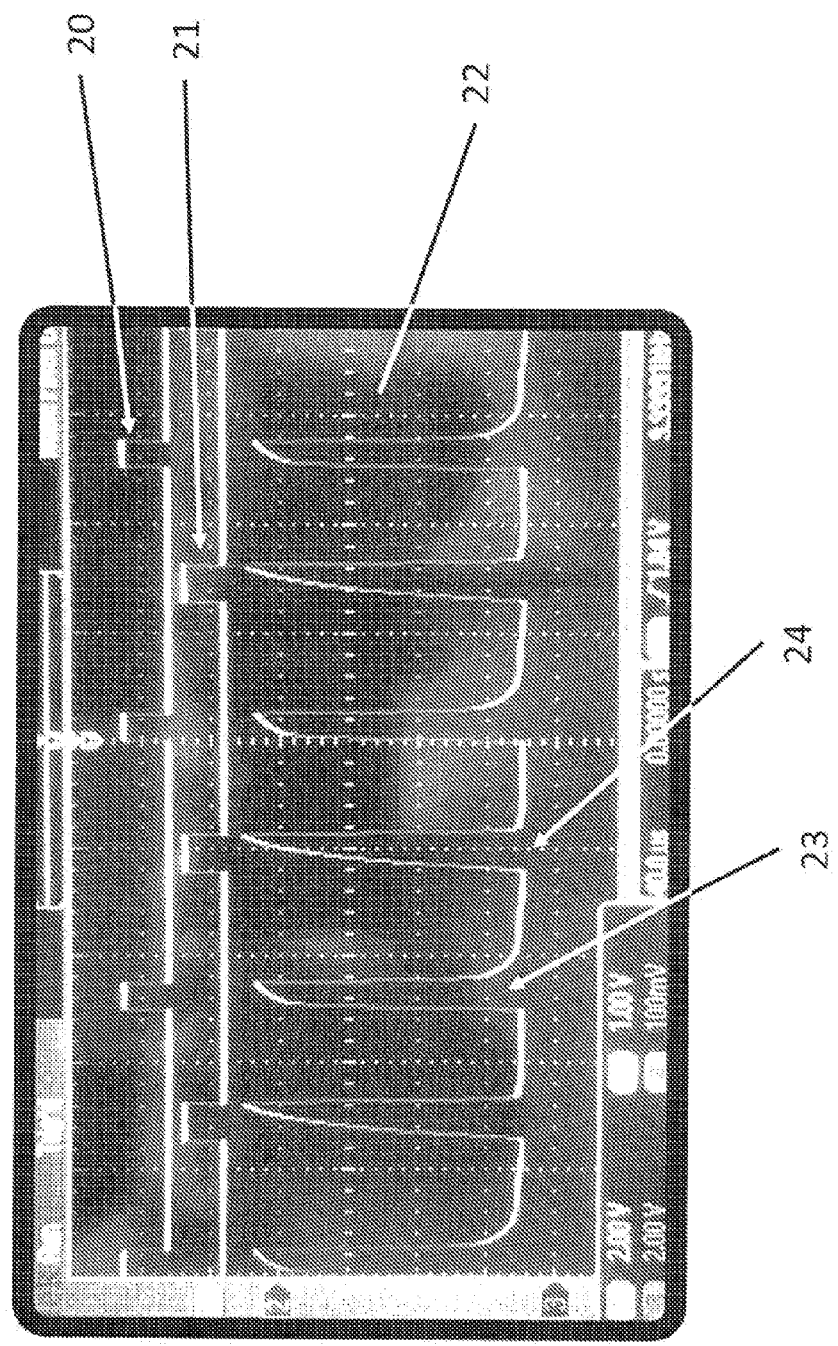
FIG. 5 illustrates the analog voltage outputs for driving the Signal and Reference diode lasers and the analog detector output for the combined laser beam prior to digitization.

FIG. 5 portrays the analog output as monitored by oscilloscope 18 (see FIG. 4). As shown in FIG. 5, the top two traces 20 and 21 of the oscilloscope display are voltage pulses 2 and 3 generated alternately and successively by high speed waveform generator 1 for driving respectively Signal diode laser 4 and Reference diode laser 5 (see FIG. 1). The bottom trace 22 of the oscilloscope display shows alternately the analog outputs of Signal laser beam 23 and Reference laser beam 24 from infrared detector 14 (see FIG. 3).

The processing of the digital data received by the computer from the infrared detector after initial data manipulation goes as follows. When both the Signal and Reference channels are pulsed at N Hz (N>10$^4$) for a measurement time period "t", where "t" is in seconds, there will be N×t Signal channel outputs and an equal number of Reference channel outputs generated by the infrared detector. A ratio value "R" is calculated for each generated Signal channel output and the corresponding Reference channel output, namely R=Signal output/Reference output. For the N×t ratio values of R calculated over the measurement time period 't', an average, namely $R_{ave}(t)$, is calculated. The calculated value of $R_{ave}(t)$ represents the measurement signal for the average concentration level of particles in the liquid in the time period "t". It is important to note that the signal to noise (S/N) for the measurement value of $R_{ave}(t)$ versus the average concentration level of particles in the liquid is a function of the value of the preselected time period "t". The longer the preselected measurement time period "t", the noise in the value of $R_{ave}(t)$ is smaller as there are more collected data to be averaged for the measurement value of it.

Figure 6:
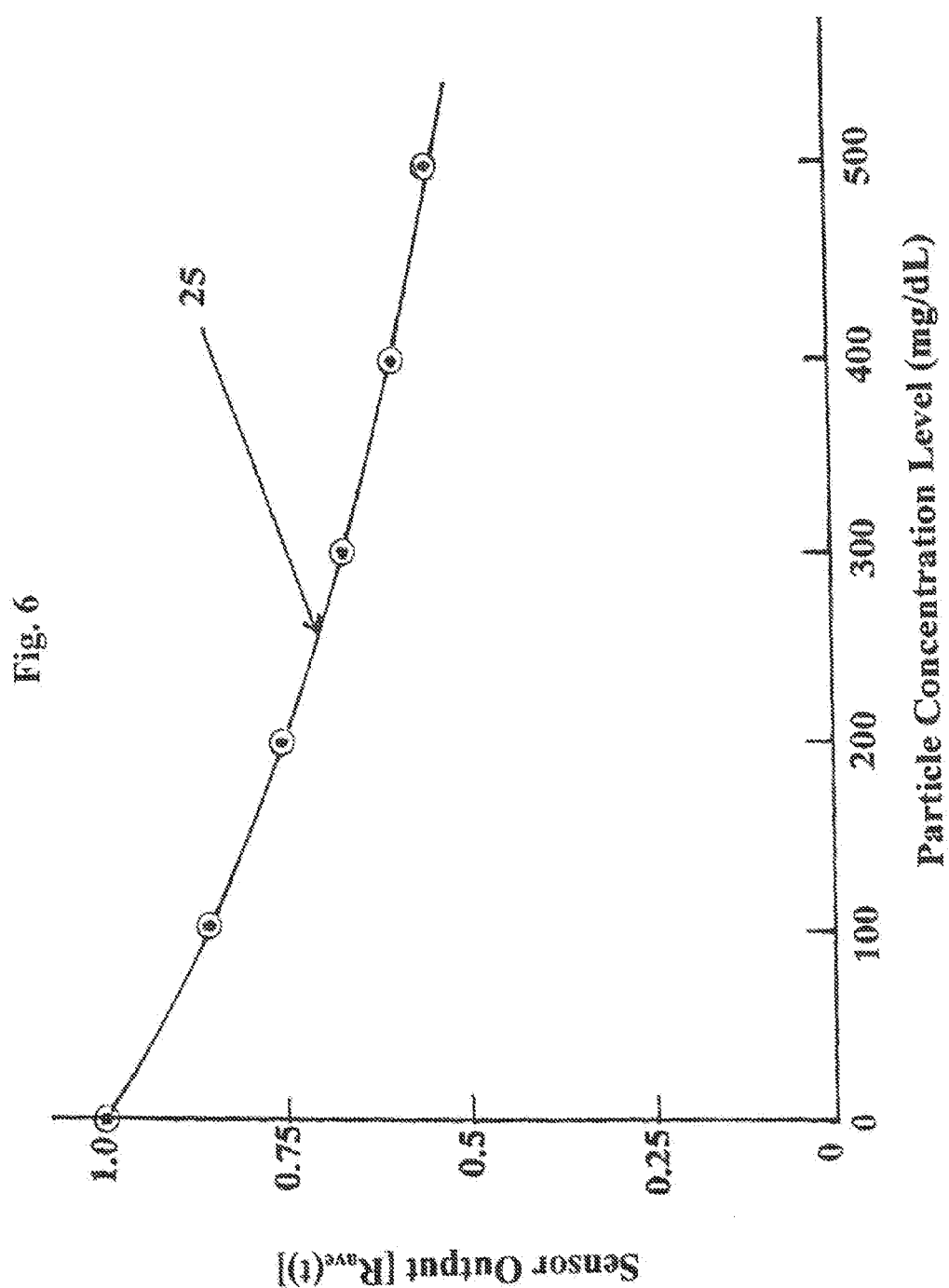
FIG. 6 illustrates a calibration curve for an NDIR liquid sensor depicting the sensor output ratio $R_{ave}(t)$ for the Signal and the Reference beams as a function of the particle concentration levels in liquid measured in milligram per 100 c.c. (mg/dL).

FIG. 6 shows graph 25 depicting the value of $R_{ave}(t)$ for a particular preselected measurement time period "t" as a function of the averaged particle concentration level "D" in the liquid measured in milligram per 100 cc (mg/dL). As can be seen in FIG. 6, the graph 25 is in essence the calibration curve of the particle concentration level for the NDIR liquid sensor. Such a calibration curve is attained by first selecting a liquid wherein different concentrations of particular particles in it are to be determined. Samples possessing different particle concentration levels in the liquid are then prepared. A measurement time period "t" is next selected for the calibration. By executing the four steps elucidated earlier for the measurement procedure, the values of $R_{ave}(t)$ are determined for each sample concentration in the liquid. The graph 25 as depicted in FIG. 6 portrays the value of $R_{ave}(t)$ as a function of the concentration levels of particles in the liquid with a preselected measurement time period "t".

Figure 7:
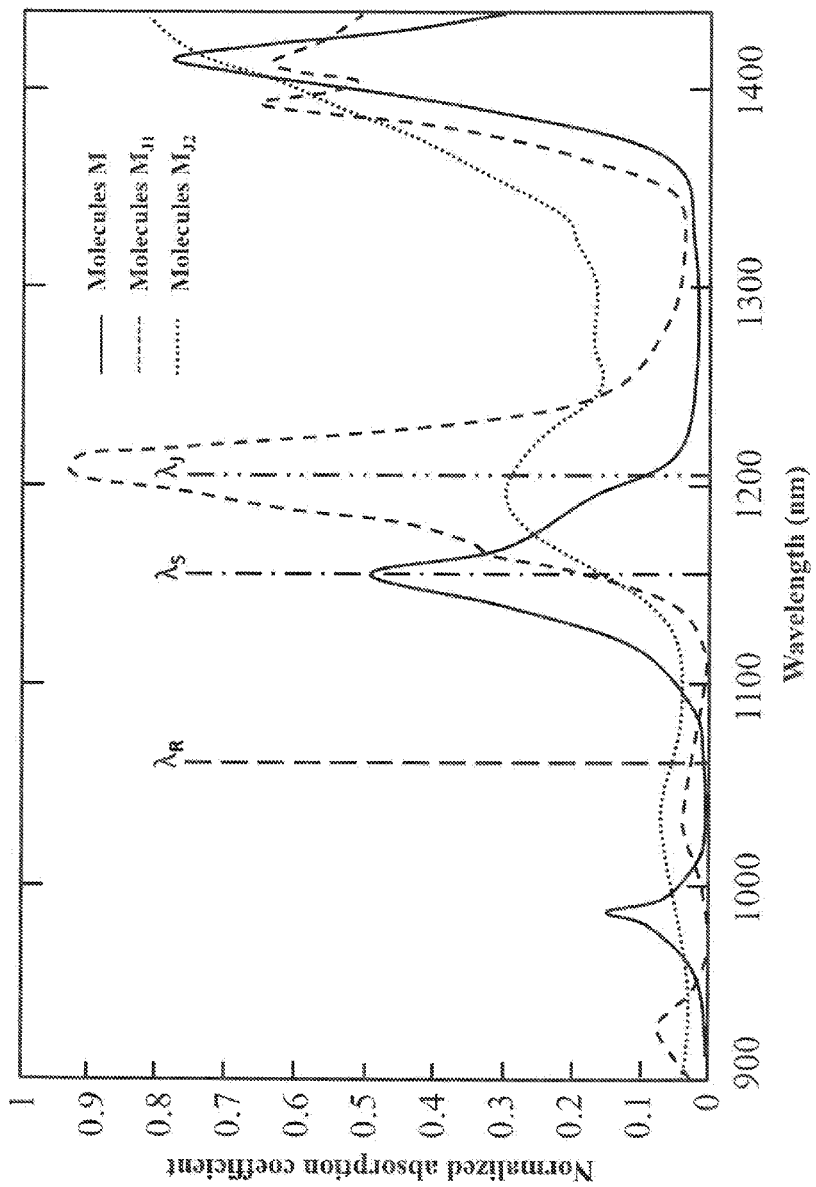
FIG. 7 shows the normalized absorption coefficients for targeted molecules M and interference molecules $M_J$ ($M_{J1}$ and $M_{J2}$) as a function of wavelength.

Now that the inventive concepts disclosed in U.S. Pat. No. 9,606,053 have been reviewed, the present invention will deal with another noise source present when the NDIR measurement technique is used to detect molecules in the liquid phase in a complex solution in which targeted molecules are admixed with molecules of some other kinds having the same absorption band signature or an absorption band signature very close to that of the targeted molecule as illustrated in FIG. 7. As shown in FIG. 7, the targeted molecule M has an absorption band at 1,150 nm ($\lambda_S$) and interfering molecules $M_J$ ($M_{J1}$ and $M_{J2}$) have an absorption band at ~1,200 nm ($\lambda_S$) and overlapping $\lambda_S$. In such a case, the interference molecules $M_{J1}$ and $M_{J2}$ will generate Absorption Interference Noise (AIN) impacting the transmittance measurement for targeted molecules M unless it is mitigated.

According to the Beer-Lambert law, the transmission of light at a particular wavelength $\lambda S$ through a medium such as a liquid phase is expressed as:

$$I=I_0 e^{-OD}; \; T=I/I_0; \; \alpha=1-T \text{ and } OD=\text{Log}_e(1/T) \tag{1}$$

where $I_0$ is the initial light intensity, I is the intensity after passing through the medium, T is the transmittance, $\alpha$ is the absorption coefficient and OD is the Optical Depth. When there is more than one type of molecule present in the liquid sample, the total absorption or composite transmittance at wavelength $\lambda_S$ through the sample is related to the summation of the individual optical depths of the molecules as follows:

$$OD(\lambda_S)_{total}=\text{Log}_e[1/T_{total}(\lambda_S)]=[C_1\alpha_1+C_2\alpha_2+\ldots]\times L \tag{2}$$

where $OD(\lambda_S)_{total}$ is the total optical depth, $C_i$ and $\alpha_i$ are respectively the molecular concentration and absorption coefficient of different molecules "i" and L is the common optical path or sample cell path length.

Equation (2) above implies that there exists a unique relationship among the quantities $T_M(\lambda_S)$, the transmittance; $C_M$, the concentration of targeted molecules M and $\alpha_M(\lambda_S)$, the absorption coefficient of the targeted molecules M in the liquid sample. Furthermore, the absorption coefficient of targeted molecules M and those of the admixed interfering molecules $M_J$ in the liquid sample appear separately as individual parts in the measured total transmittance, namely:

$$T_{total}(\lambda_S) = \alpha_M(\lambda_S) + \alpha_{MJ}(\lambda_S) \tag{3}$$

This knowledge is utilized to calibrate the concentration of the targeted molecules M versus the measured total transmittance of the liquid sample and free from AIN.

Consider the case when targeted molecules M have an absorption band with Center Wavelength (CWL) located at $\lambda_S$ in a liquid sample and its concentration $C_M$ is to be determined optically via its absorption coefficient $\alpha_M(\lambda_S) = [1 - T_M(\lambda_S)]$, where $T_M(\lambda_S)$ is the transmittance measured at $\lambda_S$, and coexisting with the targeted molecule M are different types of molecules $M_J$ which have absorption bands overlapping wavelength $\lambda_S$. Under this situation, molecules $M_J$ will create Absorption Interference Noise (AIN) to the transmittance measurement at $\lambda_S$ for determining the absorption coefficient $\alpha_M(\lambda_S) = [1 - T_M(\lambda_S)]$ for the targeted molecules M.

By selecting and utilizing an additional near infrared Interference beam with wavelength $\lambda_J$ at a spectral location where an absorption band of one or more interfering molecules $M_J$ exists while at the same time overlapping $\lambda_S$, a calibration process is developed effecting the suppression of the Absorption Interference Noise (AIN). By performing a transmittance measurement at $\lambda_J$, only the absorption coefficient of interfering molecules $M_J$, namely $\alpha_{MJ}(\lambda_J)$, is being measured. The absorption coefficient of interfering molecules $M_J$ at $\lambda_S$, namely $\alpha_{MJ}(\lambda_S)$, is not affected. However, the measured absorption coefficients $\alpha_{MJ}(\lambda_S)$ and $\alpha_{MJ}(\lambda_J)$ are proportional to each other independent of the kind and number of interfering molecules present in the liquid sample. Their relative values depend only upon their absorption strength at the two different wavelengths $\lambda_J$ and $\lambda_S$. In other words, $\alpha_{MJ}(\lambda_S)$ changes only if $\alpha_{MJ}(\lambda_J)$ changes.

If the transmittance is measured at $\lambda_J$ at the same time as $T_{total}(\lambda_S)$, is measured at $\lambda_S$ and the value of $\alpha_{MJ}(\lambda_J)$ remains unchanged, then $\alpha_{MJ}(\lambda_S)$ is basically a constant as is evident from equation (3). This knowledge is utilized to calibrate the concentration of the targeted molecules M versus the measured total transmittance of the liquid sample at $\lambda_S$ and free from AIN. This operation is valid if, as the concentration of the targeted molecules M in the liquid sample is varied, the kind and number of interfering molecules $M_J$ remain unchanged in the liquid sample, hence $\alpha_{MJ}(\lambda_J)$ is a constant and so is $\alpha_{MJ}(\lambda_S)$. Consequently, for this situation, it is possible to arrive at a calibration curve for the concentration of targeted molecules M in a liquid sample free from AIN as a function of their absorption coefficients, namely $\alpha_M(\lambda_S)$, via the measured total transmittance $T_{total}(\lambda_S)$ at $\lambda_S$ as stated in equation (3) with $\alpha_{MJ}(\lambda_S)$ being a constant.

Figure 8:
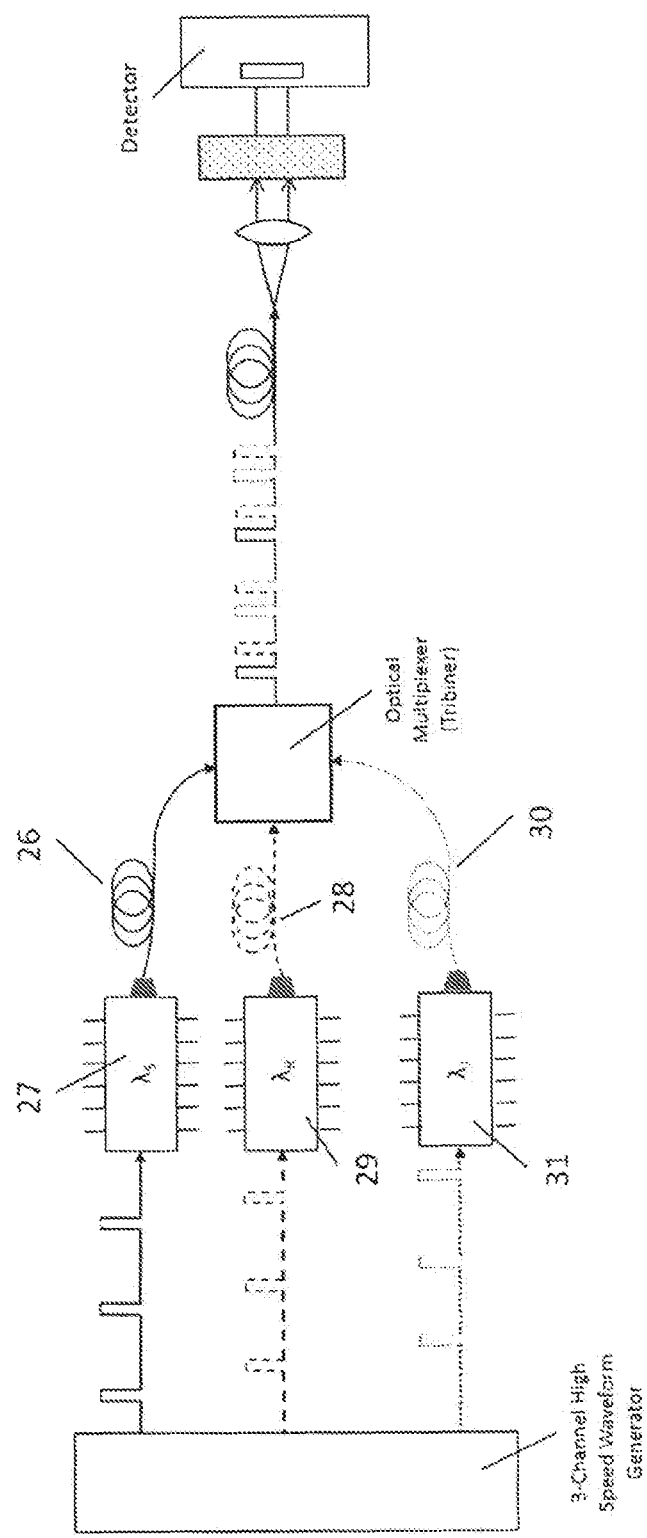
FIG. 8 shows an optical setup illustrating how a Signal diode laser, a Reference diode laser and an Interference diode laser are driven alternately and successively by a 3-channel high speed waveform generator.

FIG. 8 is an optical setup illustrating how a Signal diode laser, a Reference diode laser and an Interference diode laser are driven alternately and successively in groups of two by a 3-channel high speed waveform generator. As shown in FIG. 7, output 26 of Signal diode laser 27 is driven alternately and successively with output 28 of Reference diode laser 29 as a pair; meanwhile output 30 of Interference diode laser 31 is driven alternately and successively with output 28 of Reference diode laser 29 as another pair. This is carried out in order that the transmittance can be measured at $\lambda_S$ at essentially the same time as it is measured at $\lambda_J$, so that both will have essentially the same scattering noise reduction. The rest of the optical and electronic processing system setup for a three diode laser system to suppress both scattering noise and AIN is the same as the two diode laser system disclosed in U.S. Pat. No. 9,606,053 (2017) for suppressing just the scattering noise.

Starting out with a very low concentration $C_0$ of molecules M determined and verified chemically in a liquid sample admixed with several different kinds of interfering molecules $M_J$, small stepwise concentration increments $\Delta_i$ (where "i" is an integer greater than zero), of M molecules are successively added to it. A transmittance measurement at signal wavelength $\lambda_S$ is made before every concentration increment in order to obtain respective absorption coefficient values for each concentration level as follows:

$$C_0: \alpha_{MC0}(\lambda_S) + \alpha_{MJ}(\lambda_S) = K_1 \tag{C1}$$

$$C_1 = C_0 + \Delta_1: \alpha_{MC1}(\lambda_S) + \alpha_{MJ}(\lambda_S) = K_2 \tag{C2}$$

$$C_2 = C_1 + \Delta_2: \alpha_{MC2}(\lambda_S) + \alpha_{MJ}(\lambda_S) = K_3 \tag{C3}$$

...

$$C_N = C_{N-1} + \Delta_N: \alpha_{MCN}(\lambda_S) + \alpha_{MJ}(\lambda_S) = K_{N+1} \tag{$C_{N+1}$}$$

where $\alpha_{MCi}(\lambda_S)$ and $\alpha_{MJ}(\lambda_S)$ are, respectively, the absorption coefficient of targeted molecules M and those of the admixed interfering molecules $M_J$ at $\lambda_S$ and $K_1, K_2, \ldots K_{N+1}$ are measured total transmittance values reflecting the respective absorption coefficients. Note that $\alpha_{MJ}(\lambda_S)$ is in essence the sum of the absorption coefficients for all admixed interfering molecules overlapping at $\lambda_S$ in the liquid sample which stay unchanged during the entire calibration operation.

From the above data compilation, one obtains:

$$\text{Concentration } \Delta_1: \alpha_{M\Delta 1}(\lambda_S) = \alpha_{MC1}(\lambda_S) - \alpha_{MC0}(\lambda_S) = K_2 - K_1 \tag{D1}$$

$$\text{Concentration } \Delta_1 + \Delta_2: \alpha_{M[\Delta 1 + \Delta 2]}(\lambda_S) = \alpha_{MC2}(\lambda_S) - \alpha_{MC0}(\lambda_S) = K_3 - K_1 \tag{D2}$$

$$\text{Concentration } \Delta_1 + \Delta_2 + \Delta_3: \alpha_{M[\Delta 1 + \Delta 2 + \Delta 3]}(\lambda_S) = \alpha_{MC3}(\lambda_S) - \alpha_{MC0}(\lambda_S) = K_4 - K_1 \tag{D3}$$

...

$$\text{Concentration } \Delta_1 + \Delta_2 + \ldots + \Delta_N: \alpha_{M[\Delta 1 + \Delta 2 + \ldots + \Delta N]}(\lambda_S) = \alpha_{MC3}(\lambda_S) - \alpha_{MC0}(\lambda_S) = K_{N+1} - K_1 \tag{DN}$$

Since the values for $K_1$ through $K_{N+1}$ are measured and known quantities and the values of $\Delta_1$ to $\Delta_N$ are a priori quantities measured and verified by other methods, equations (D1) to (DN) above constitute an experimentally determined calibration curve as shown in FIG. 9 for molecules M in the liquid sample without AIN generated by admixed molecules $M_J$. This calibration curve plots the measured and verified concentration range of molecules M in the liquid sample from $\Delta_1$ to $\Delta_N$ versus the measured absorption coefficients $\alpha_{M\Delta 1}(\lambda_S)$ to $\alpha_{M[\Delta 1 + \Delta 2 + \ldots \Delta N]}(\lambda_S)$ for molecules M in the liquid sample without Absorption Interference Noise (AIN). For an unknown concentration of molecules M admixed with interfering molecules $M_J$ in a liquid sample, one merely has to measure the total transmittance of the liquid sample to arrive at the absorption coefficient value. The calibration curve derived above (see FIG. 9) can then be looked up to obtain the unknown optically determined concentration value.

The independent transmittance measurement of $\alpha_{MJ}(\lambda_J)$ has another very important function when it is not used to verify the validity of a calibration operation. Assuming that a sensor is available and is designed based upon the current invention, there is no way a user of the sensor knows whether or not the sensor stays functionally calibrated and accurate. However, if the value for $\alpha_{MJ}(\lambda_J)$ is stored in the sensor during calibration before it is released for use, the accuracy of the sensor can be checked at any time before use to find out whether the stored value of $\alpha_{MJ}(\lambda_J)$ has changed under the initial calibration condition. If this value changes, then the sensor might need to be recalibrated before it is used again.

Note that the procedure just set forth for dealing with admixed molecules $M_J$ might be varied, if need be, to deal with one or more additional admixed molecules $M_{J+X}$ by selecting and utilizing additional near infrared Interference beam(s) X with wavelength(s) $\lambda_X$. Also, in designing the pulse sequence of various beams, variations to pulse sequencing can be made, in less desirable configurations, so long as the frequency and sequence of pulses is such that unwanted scattering noise is not introduced to compromise the overall measurement results.

The procedure for dealing with a complex solution in which targeted molecules are admixed with molecules of some other kinds having the same absorption band signature or an absorption band signature very close to that of the targeted molecule will now be applied as an example to measuring glucose in a blood sample.

As disclosed in earlier filed U.S. Ser. No. 15/444,136, in the near infrared (NIR) spectral region, glucose has an overtone absorption band located at 1,150 nm which can be used as the center wavelength for the signal beam. This absorption band is desirable because it has a water absorption coefficient of no greater than ~1.0 $cm^{-1}$, which is especially preferred, as it helps to minimize effects created by water absorption. A reference beam wavelength of 1,064 nm, where there is no glucose molecule absorption, can be used as the center wavelength for the reference beam. Therefore, by using a pulse frequency of 10 KHz or more, 1,150 nm as the center wavelength for the signal beam with a relatively narrow bandwidth (+/−a few nm) and 1,060 nm as the center wavelength for the reference beam with also a relatively narrow bandwidth, one is able to detect glucose molecules in blood with minimum scattering noise.

Detection of glucose molecules in blood has long faced a very serious accuracy problem due to the presence of many interfering molecules coexisting with glucose in blood. Furthermore, the kind and number of these interfering molecules present also change with time. These interfering molecules include lipids, fatty acids, melanin, collagen, hormones, etc. to name just a few. The present invention specifically formulates a method to deal with Absorption Interference Noise caused by interfering molecules by treating them as a group rather than as individual interfering molecules. The simplest way to utilize the present invention to deal with this problem is to just add a third Interference beam in order to obtain the value of their absorption coefficients as a sum via the measurement of their total transmittance at the wavelength of the selected Interference beam. This method allows the calibration curve of glucose molecules in blood to be established as a function of its concentration via its measured total transmittance. Meanwhile the value of the measured transmittance of the representative group of interfering molecules at the selected wavelength of the Interference beam $\lambda_J$ serves as a potent parameter for validating the procured calibration curve. Consistent with the earlier filed disclosure of U.S. Ser. No. 15/444,136, an excellent choice for the wavelength of the Interference beam is at $\lambda_J$=1,210 nm.

If the measured glucose level of the user is not as expected, then two possibilities might exist. The first one is that the sensor is no longer working properly and needs to be examined and remedied. If the sensor is checked out and found to be working properly, the second possibility is that the glucose level of the patient has indeed changed and needs immediate medical attention. The stored value for $\alpha_{MJ}(\lambda_J)$ during calibration of the sensor can be used as a parameter to indicate whether or not the glucose sensor is functioning properly.

Finally, it must be pointed out that there is a fundamental difference between the glucose concentration level determined chemically by a finger prick blood measure and that indirectly determined by an optical method using measured total transmittance to arrive at an absorption coefficient value. The finger prick method measures the glucose level in blood whereas the optical method measures the glucose level in body interstitial fluid. But since the current calibration method uses the chemically determined glucose level as the standard reference for the optical measurement, this fundamental difference between the two methods effectively washes out.

While the invention has been described herein with reference to a preferred embodiment, this embodiment has been presented by way of example only, and not to limit the scope of the invention. Additional embodiments thereof will be obvious to those skilled in the art having the benefit of this detailed description. For example, different combinations of devices can be used to generate a collimated beam used in the present invention, such as multiple multiplexers, without departing from the spirit of the present invention. Further modifications are also possible in alternative embodiments without departing from the inventive concept.

What is claimed is:

1. A process for determining a concentration of a targeted molecule M within a given time period in a liquid sampling matrix in which at least one interfering molecule $M_J$ coexists with the targeted molecule, comprising the steps of:

pulsing infrared radiation from a signal source, an interference source and a reference source into a multiplexer and collimating radiation leaving the multiplexer into a pulsed beam which is directed through the liquid sampling matrix;

detecting infrared radiation by a detector as a pulsed signal and reference channel output and a pulsed interference signal and reference channel output from the pulsed beam after it passes through the liquid sampling matrix;

using signal processing to obtain an average ratio value of $R_{ave}(t)$ for a first preselected period of time ("t") from the pulsed signal and reference channel output, where $R_{ave}(t)$=signal channel/reference channel output for the first preselected period of time;

using signal processing to obtain an average ratio value of $R_{Jave}(t_2)$ for a second preselected period of time ("$t_2$") from the pulsed interference and reference channel output, where $R_{Jave}(t_2)$=interference channel/reference channel output for the second preselected period of time;

using $R_{Jave}(t_2)$ determine that a calibration curve is valid for the given time period;

if the calibration curve is valid, using electronics to calculate the concentration of the targeted molecule M in the liquid sampling matrix by use of $R_{ave}(t)$ and the calibration curve; and providing the concentration of the targeted molecule M in the liquid sampling matrix as an output from said electronics;

wherein the signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band;

wherein said at least one interfering molecule $M_J$ absorbs radiation at the signal wavelength;

wherein the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency.

2. The process of claim 1, wherein the pulsed beam is comprised of an alternate and sequential pulsing of a repeating pattern of the signal source, followed by the reference source, followed by the interference source, followed by the reference source.

3. The process of claim 1, wherein the pulsed beam is comprised of an alternate and sequential pulsing of a repeating pattern of the signal source, the reference source and the interference source.

4. The process of claim 1, wherein the frequency of N Hz is greater than 1.0 KHz with a duty factor of at least 10%.

5. The process of claim 1, wherein $t=t_2$.

6. The process of claim 1, wherein the signal beam has a signal beam center wavelength of 1,150 nm (1.150μ) and the reference beam has a center wavelength of 1,064 nm (1.064μ).

7. The process of claim 6, wherein the interference beam has a center wavelength of 1,210 nm.

8. The process of claim 7, wherein the targeted molecule M is glucose.

9. The process of claim 8, wherein said at least one interfering molecule $M_J$ is comprised of a plurality of interfering molecules contained in a body interstitial fluid.

* * * * *